US012736467B2

(12) United States Patent
Sayama

(10) Patent No.: US 12,736,467 B2
(45) Date of Patent: Sep. 15, 2026

(54) SPECTROSCOPIC APPARATUS AND GAS DETECTION APPARATUS

(71) Applicant: Tamron Co., Ltd., Saitama (JP)

(72) Inventor: Atsushi Sayama, Saitama (JP)

(73) Assignee: TAMRON CO., LTD., Saitama (JP)

( * ) Notice: Subject to any disclaimer, the term of this patent is extended or adjusted under 35 U.S.C. 154(b) by 83 days.

(21) Appl. No.: 19/043,534

(22) Filed: Feb. 3, 2025

(65) Prior Publication Data

US 2025/0290849 A1 Sep. 18, 2025

(30) Foreign Application Priority Data

Mar. 13, 2024 (JP) ................................ 2024-039375

(51) Int. Cl.
*G01N 21/3504* (2014.01)
*G01N 21/359* (2014.01)
*G01N 33/497* (2006.01)

(52) U.S. Cl.
CPC ....... *G01N 21/3504* (2013.01); *G01N 21/359* (2013.01); *G01N 33/497* (2013.01); *G01N 2201/062* (2013.01); *G01N 2201/0636* (2013.01)

(58) Field of Classification Search
CPC ............ G01N 21/3504; G01N 21/359; G01N 33/497; G01N 2201/062; G01N 2201/0636
See application file for complete search history.

(56) References Cited

U.S. PATENT DOCUMENTS

2004/0211905 A1 10/2004 Hancock et al.
2015/0289782 A1 10/2015 Peverall et al.
2016/0054220 A1* 2/2016 Nishijima ........... G01N 21/359 356/409
2016/0327475 A1 11/2016 Hayashi et al.
2018/0259452 A1 9/2018 Li et al.
2020/0319093 A1 10/2020 Purves et al.

FOREIGN PATENT DOCUMENTS

JP 2005-501233 A 1/2005
JP 2016-502077 A 1/2016
JP 2017-502303 A 1/2017
JP 2020-509350 A 3/2020
JP 2022-529621 A 6/2022

OTHER PUBLICATIONS

Zheng et al., Near-infrared broadband cavity-enhanced sensor system for methane detection using a wavelet-denoising assisted Fourier-transform spectrometer, CLEO 2019, Jan. 2019, pp. 1-2.
Zheng et al., Near-Infrared Broadband Cavity-Enhanced Spectroscopic Multigas Sensor Using a 1650 nm Light Emitting Diode, ACS Sensors, Jun. 2019, pp. 1-10.

* cited by examiner

*Primary Examiner* — Mark R Gaworecki
(74) *Attorney, Agent, or Firm* — Paratus Law Group, PLLC

(57) ABSTRACT

A gas detection apparatus includes a spectroscopic apparatus and a gas supply pipe, the spectroscopic apparatus including a light source of near-infrared light having a specified full width at half maximum in the wavelength spectrum, an optical cavity having a pair of reflectors facing each other and having a specific effective reflectivity, and a photodetector that detects intensity of emission light from the optical cavity.

7 Claims, 12 Drawing Sheets

SPECTROSCOPIC APPARATUS AND GAS DETECTION APPARATUS

CROSS-REFERENCE TO RELATED APPLICATIONS

This application is based on and claims the benefit of priority from Japanese Patent Application No. 2024-039375, filed on Mar. 13, 2024, the entire contents of which are incorporated herein by reference.

BACKGROUND OF THE INVENTION

Technical Field

The present invention relates to a spectroscopic apparatus and a gas detection apparatus.

Related Art

In recent years, it is becoming clear that the concentration of a specific component contained in a gas (exhaled air, skin gas, intestinal gas, etc.) called biological gas emitted from a human body correlates with a specific medical condition. The concentration of the gas component changes in an extremely low-concentration region of ppb (pert per billion, 1/1 billion) to ppm (pert per million, 1/1 million) in terms of a volume ratio. As a technique for quantitatively detecting such an extremely low-concentration gas, cavity-enhanced absorption spectroscopy can be mentioned. The spectroscopic method is a method in which an effective optical path length is increased by light reciprocating many times between reflectors by a configuration in which two reflectors having high reflectivity are opposed to each other (also referred to as an "optical cavity"), and absorption of light by an extremely low-concentration gas is enhanced.

As a technique for detecting a specific gas component in exhaled air by cavity-enhanced absorption spectroscopy, a technique for detecting carbon dioxide in exhaled air using a laser light source and an optical cavity (see, for example, JP 2005-501233 A), a technique for quantitatively detecting ketone such as acetone in exhaled air using an ultraviolet light emitting diode (LED) and an optical cavity (see, for example, JP 2016-502077 A), a technique for determining the degree of lung cancer from an exhaled air sample using a laser light source and an optical cavity (see, for example, JP 2022-529621 A), a technique for performing exhaled air analysis by multipath spectroscopy using an ultraviolet LED (see, for example, JP 2020-509350 A), and a technique for detecting oxygen by multipath spectroscopy using an LED light source or a laser diode of a specific wavelength from ultraviolet to near-infrared (see, for example, JP 2017-502303 A) are known.

As a technique for detecting a specific trace amount of gas components by cavity-enhanced absorption spectroscopy, cavity-enhanced absorption spectroscopy using a near-infrared LED light source (for example, see Kaiyuan Zheng et. al., Near-Infrared Broadband Cavity-Enhanced Spectroscopic Multigas Sensor Using a 1650 nm Light Emitting Diode, [online], 2019, <URL:https://www.researchgate.net/publication/333705294>) and cavity-enhanced absorption spectroscopy using a halogen lamp light source (for example, see Kaiyuan Zheng et. al., Near-infrared broadband cavity-enhanced sensor system for methane detection using a wavelet-denoising assisted Fourier-transform spectrometer, [online], 2019, <URL:https://www.researchgate.net/publication/332917977>) are known.

SUMMARY OF THE INVENTION

However, the conventional technique as described above has various practical problems. As one of such practical problems, there is a problem that the cost increases. For example, the laser light source itself is expensive. In addition, for example, in the case of using a laser light source, it is necessary to precisely adjust the optical-cavity length with a piezo stage or the like in order to satisfy the resonance condition. In a case where it is necessary to precisely adjust the optical-cavity length in this manner, the configuration of the device becomes complicated, and the device becomes expensive. In addition, for example, when a laser light source is used, a reflector having a high reflectivity is required. A reflector having such a high reflectivity is generally of high quality, and is itself expensive. In addition, when reflective coating is applied to the entire inner surface of the gas cell constituting the optical cavity in order to increase the optical path length, a large area of coating is required, and thus the product cost increases.

In addition, the conventional technique as described above has a problem that implementation is difficult as one of practical problems. For example, in the technique that requires a reflector having a high reflectivity, the resonance condition of the optical cavity becomes stricter as the reflectivity of the reflector is higher, and high-precision optical axis adjustment and removal of disturbance such as vibration are required. Therefore, implementation becomes even more difficult. In addition, in the technique using multipath spectroscopy, it is difficult to sufficiently increase the optical path length, and the species of detectable gas is limited. Therefore, it is difficult to apply the technique to analysis of biological gas. Furthermore, it is very difficult to apply a technique using ultraviolet light as a light source. More specifically, since most organic substances generally have a broad absorption band in the wavelength range of ultraviolet light, absorption bands of different organic substances overlap each other. Therefore, it is practically difficult to analyze biological gas containing a great number of organic substances.

In addition, it is difficult to analyze biological gas by spectrometry only with data of a single wavelength, and it is desirable to acquire multi-wavelength data (spectrum). For these reasons, there is still room for study on the technique using a laser as a light source.

An object of one aspect of the present invention is to provide a technique for detecting a trace gas that suppresses an increase in cost and is highly practical.

In order to solve the above problems, a spectroscopic apparatus according to an aspect of the present invention includes: a light source that outputs near-infrared light; an optical cavity that has a pair of opposing reflectors and can supply a gas to be measured between the reflectors, and in which incident light from the light source is introduced into between the reflectors; and a photodetector that detects intensity of emission light from the optical cavity for each wavelength, in which a full width at half maximum of a wavelength spectrum of near-infrared light output from the light source and incident on the optical cavity is 15 nm or more. The spectroscopic apparatus satisfies the following formula (1) in a specific concentration change range of the gas to be measured:

[Math 1]

$$\alpha = \frac{1}{L}\left(\frac{I_0}{I} - 1\right)(1 - R) \quad (1)$$

$$R = \sqrt{R1 \times R2} \quad (2)$$

in the formula (1), α represents an absorption coefficient of the gas to be measured, L represents a distance between optical centers of the pair of reflectors, $I_0$ represents the intensity of the emission light from the optical cavity when the gas to be measured is not supplied to the optical cavity, I represents the intensity of the emission light from the optical cavity to which the gas to be measured is supplied, and R represents an effective reflectivity of the pair of reflectors represented by the formula (2), and in the formula (2), R1 represents the reflectivity of one of the pair of reflectors, and R2 represents the reflectivity of the other of the pair of reflectors.

In order to solve the above problems, a gas detection apparatus according to an aspect of the present invention includes: the aforementioned spectroscopic apparatus; and a gas supply unit that supplies the gas to be measured to the optical cavity.

According to one aspect of the present invention, it is possible to provide a technique for detecting a trace gas that suppresses an increase in cost and is highly practical.

BRIEF DESCRIPTION OF THE DRAWINGS

FIG. 8 is a diagram schematically illustrating a configuration of a spectroscopic apparatus according to the second embodiment of the present invention;

FIG. 10 is a diagram schematically illustrating a configuration of a spectroscopic apparatus according to the fourth embodiment of the present invention;

DESCRIPTION OF THE EMBODIMENTS

First Embodiment

Hereinafter, an embodiment of the present invention will be described in detail.

[Configuration]

Figure 1:
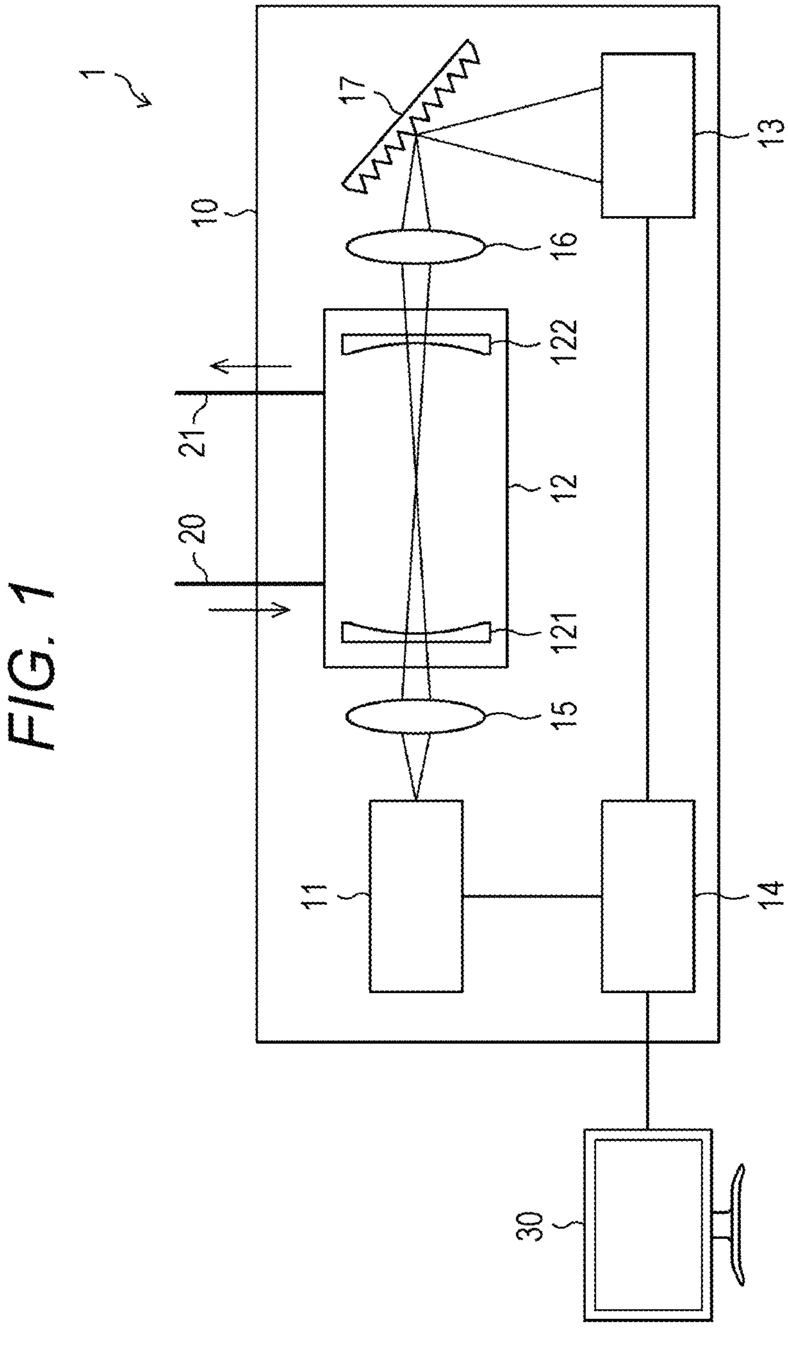
FIG. 1 is a diagram schematically illustrating a configuration of a gas detection apparatus according to the first embodiment of the present invention.

FIG. 1 schematically illustrates a configuration of a gas detection apparatus according to the present embodiment. As illustrated in FIG. 1, the gas detection apparatus 1 includes a spectroscopic apparatus 10, a gas supply pipe 20, and a display device 30.

The spectroscopic apparatus 10 includes a light source 11, an optical cavity 12, a photodetector 13, a control unit 14, focus lenses 15 and 16, and a diffraction grating 17.

The light source 11 is a light source that outputs near-infrared light, and is, for example, a near-infrared LED light source. The light source 11 outputs light (near-infrared light) having a wavelength within a range of 800-2000 nm. For example, the peak emission wavelength of the light source 11 is 1650 nm, and the full width at half maximum of the emission wavelength spectrum is 15 nm or more.

From the viewpoint of sufficiently acquiring the absorption peak of the component to be detected, the wavelength band of the emission wavelength spectrum of the light source 11 is desirably a wavelength range that is twice or more the full width at half maximum of the absorption peak of the component to be detected. From such a viewpoint, for example, when the component to be detected is acetone to be described later, the full width at half maximum of the emission wavelength spectrum may be 15 nm or more. The full width at half maximum in the emission wavelength spectrum of the light source 11 may be wider from the viewpoint of obtaining multi-wavelength data (spectrum), and may be, for example, 50 nm or more from such a viewpoint.

The optical cavity 12 is a member also referred to as a "gas cell" in the field of spectroscopic analysis, and includes a cylindrical gas chamber and a pair of reflectors 121 and 122 disposed opposite to both ends of the gas chamber. In addition, the gas chamber has a ventilation port through which the inside and the outside communicate with each other so that the gas to be measured can flow. The optical cavity 12 is thus configured to have a pair of opposing reflectors and to be able to supply a gas to be measured between the reflectors, and such that incident light from the light source is introduced into between the reflectors.

The reflectors 121 and 122 are arranged such that incident light to the optical cavity 12 reciprocates. The reflectivity of each of the reflectors 121 and 122 is lower than the reflectivity of a high-reflectivity mirror for a conventional laser light source, for example, the reflectivity of near-infrared light is less than 99.95%. The reflectivities of the reflectors 121 and 122 can be appropriately set in a range of less than 99.95% according to the optical-cavity length and the absorption cross section and concentration change range of the gas to be measured. In consideration of measurement efficiency, the reflectivity is preferably 98% or more.

The reflectivities of the reflectors 121 and 122 are set within the range of the effective reflectivity R satisfying the following formula (1) in a specific concentration change range of the gas to be measured.

[Math 2]

$$\alpha = \frac{1}{L}\left(\frac{I_0}{I} - 1\right)(1 - R) \quad (1)$$

In the formula (1), α represents an absorption coefficient of the gas to be measured. α is represented by a product of an absorption cross section and a concentration of a substance (also referred to as "component to be detected"). Since the absorption cross section is a unique value depending on the substance, the change in the absorption coefficient can be linked to the change in the concentration of the component to be detected in the gas to be measured. L is a geometric optical-cavity length and is a distance between optical centers of the reflectors 121 and 122.

In the formula (1), $I_0$ represents the intensity of the emission light from the optical cavity when the gas to be measured is not supplied to the optical cavity, and I represents the intensity of the emission light from the optical cavity where the gas to be measured is supplied. R is the effective reflectivity of the reflectors 121 and 122. The effective reflectivity R is expressed by the following formula (2).

[Math 3]

$$R = \sqrt{R1 \times R2} \quad (2)$$

In the formula (2), R1 represents the reflectivity of one of the reflectors 121, 122, and R2 represents the reflectivity of the other of the reflectors 121, 122. The reflectivities of the reflectors 121 and 122 can be appropriately determined from the amount of change in the absorption coefficient in the range of concentration change in the gas to be measured in consideration of the lower detection limit or the like actually determined from noise or the like of the spectroscopic apparatus 10.

The focus lens 15 is a lens for focusing the light from the light source 11 toward the optical cavity 12. The focus lens 16 is a lens for focusing the light leaking from the optical cavity 12 toward the rear (the diffraction grating 17 in the present embodiment). The focus lenses 15 and 16 may be lenses of the same type or may be lenses of different types. Each of the focus lenses 15 and 16 may be a single lens, or may be a variable focus lens group or the like capable of more accurately adjusting the focus position.

The diffraction grating 17 is an optical element that disperses the emission light from the optical cavity 12 into wavelength components and emits the wavelength components toward the photodetector 13.

The photodetector 13 is a detector that detects the intensity of each of the emission light components dispersed for each wavelength from the diffraction grating 17.

The photodetector 13 has detection sensitivity satisfying the intensity ratio $I_0/I$ of the emission light in the formula (1) in a specific concentration change range of the gas to be measured. Examples of the photodetector 13 include a photodiode, a photomultiplier, and a sensor such as a charge coupled device (CCD) or a complementary metal oxide semiconductor (CMOS). The photodetector 13 is preferably an array type detector from the viewpoint of detecting the intensity for each wavelength in the emission light from the optical cavity 12, and is more preferably used in combination with a diffraction grating as in the present embodiment.

Figure 2:
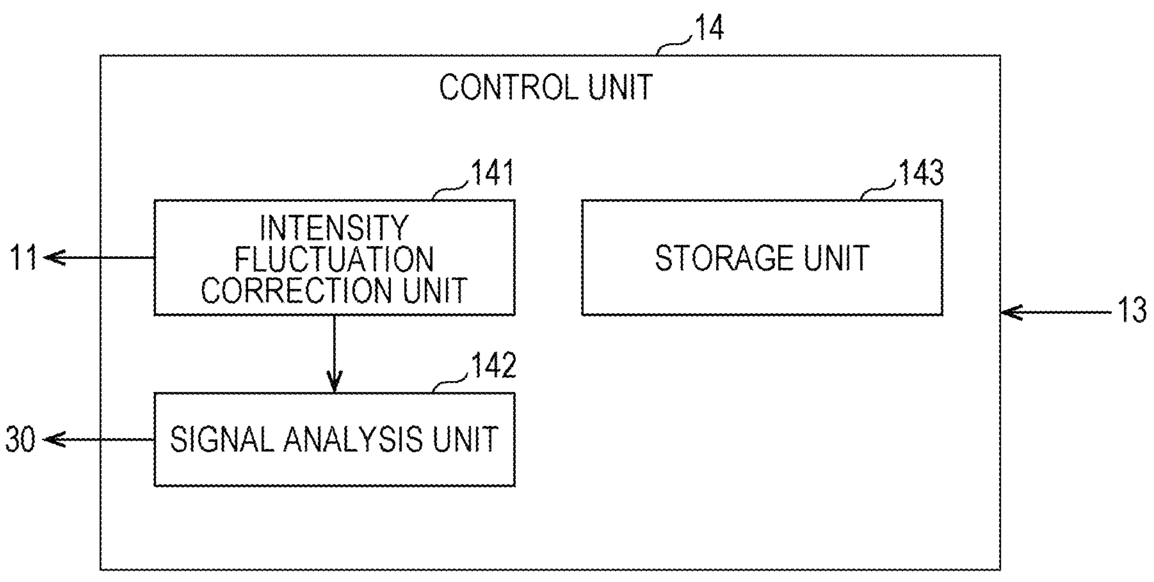
FIG. 2 is a diagram schematically illustrating an example of a functional configuration of a control unit in the first embodiment of the present invention.

An example of a functional configuration of the control unit 14 is schematically illustrated in FIG. 2. As illustrated in FIG. 2, the control unit 14 includes an intensity fluctuation correction unit 141, a signal analysis unit 142, and a storage unit 143. The function of the control unit 14 will be described later.

The gas supply pipe 20 is connected to one of the two above-described ventilation ports provided in the optical cavity 12. The gas supply pipe 20 is a pipe for supplying biological gas as the gas to be measured to the optical cavity 12, and is, for example, a collection pipe for blowing exhaled air by the subject. The gas exhaust pipe 21 is connected to the other ventilation port of the optical cavity 12. The gas supply pipe 20 and the gas exhaust pipe 21 each include, for example, an on-off valve and are openable and closable.

The display device 30 is a device capable of displaying an image, and is, for example, a liquid crystal display device.

[Description of Gas Analysis]

Hereinafter, gas analysis according to the present embodiment will be described. In general, the absorbance in the analysis by the absorbance of the gas is represented by the following formula (3) (Lambert-Berr's law).

[Math 4]

$$A = -\log\frac{I}{I_{in}} \propto \sigma(\lambda) \times N \times L \quad (3)$$

In the formula (3), A represents absorbance, $I_{in}$ represents intensity of light incident on the optical cavity, I represents intensity of emission light from the optical cavity, σ represents an absorption cross section ($m^2$/mol) of a molecule (component to be detected) in the gas to be measured, λ represents a wavelength of the incident light, N represents a number density (mol/$m^3$) of the molecule, and L represents an optical-cavity length (m). According to the formula (3), it is found that it is effective to increase the optical path length in order to increase the absorbance. In general, in order to increase the optical path length, it is effective that the reflectivity of the pair of reflectors in the optical cavity is high.

On the other hand, in order to accumulate a sufficient amount of light in the optical cavity and leak the light from the optical cavity, it is necessary to satisfy a resonance condition (a condition that a standing wave rises) so that light reciprocating in the optical cavity does not cancel each other. In order to satisfy the resonance condition in the optical cavity, it is necessary to satisfy the following formula (4). In the formula (4), n is any natural number. As shown in the formula (4), it is necessary for satisfying the resonance condition that the optical path length of the light reciprocating in the optical cavity is an integral multiple of the wavelength of the light.

[Math 5]

$$2L = n\lambda \quad (4)$$

In the case of a laser light source, since the laser light source is generally monochromatic light, it is necessary to strictly adjust the optical-cavity length by a piezo stage or the like in order to satisfy the resonance condition. It is also important to eliminate disturbances such as vibrations and temperature changes.

When a laser light source is used as the light source, for example, a reflector having a high reflectivity of 99.99% is used, and various conditions including the optical-cavity length are strictly set as described above, whereby data at one wavelength can be obtained. In order to acquire a spectrum (multi-wavelength data), a plurality of light sources or a wavelength sweep is required, and a device for realizing the same becomes complicated and a cost of the device increases.

When an LED is used as a light source instead of the laser light source under the condition of using the laser light source, it is confirmed that the LED is not applied to the measurement of trace components in the gas because the SN ratio is low. It is considered that this is because incident light into the optical cavity is reflected by the surface, is not sufficiently introduced into the optical cavity, is lost due to scattering of light in the optical cavity or the like, and is not sufficiently accumulated in the optical cavity.

Figure 3:
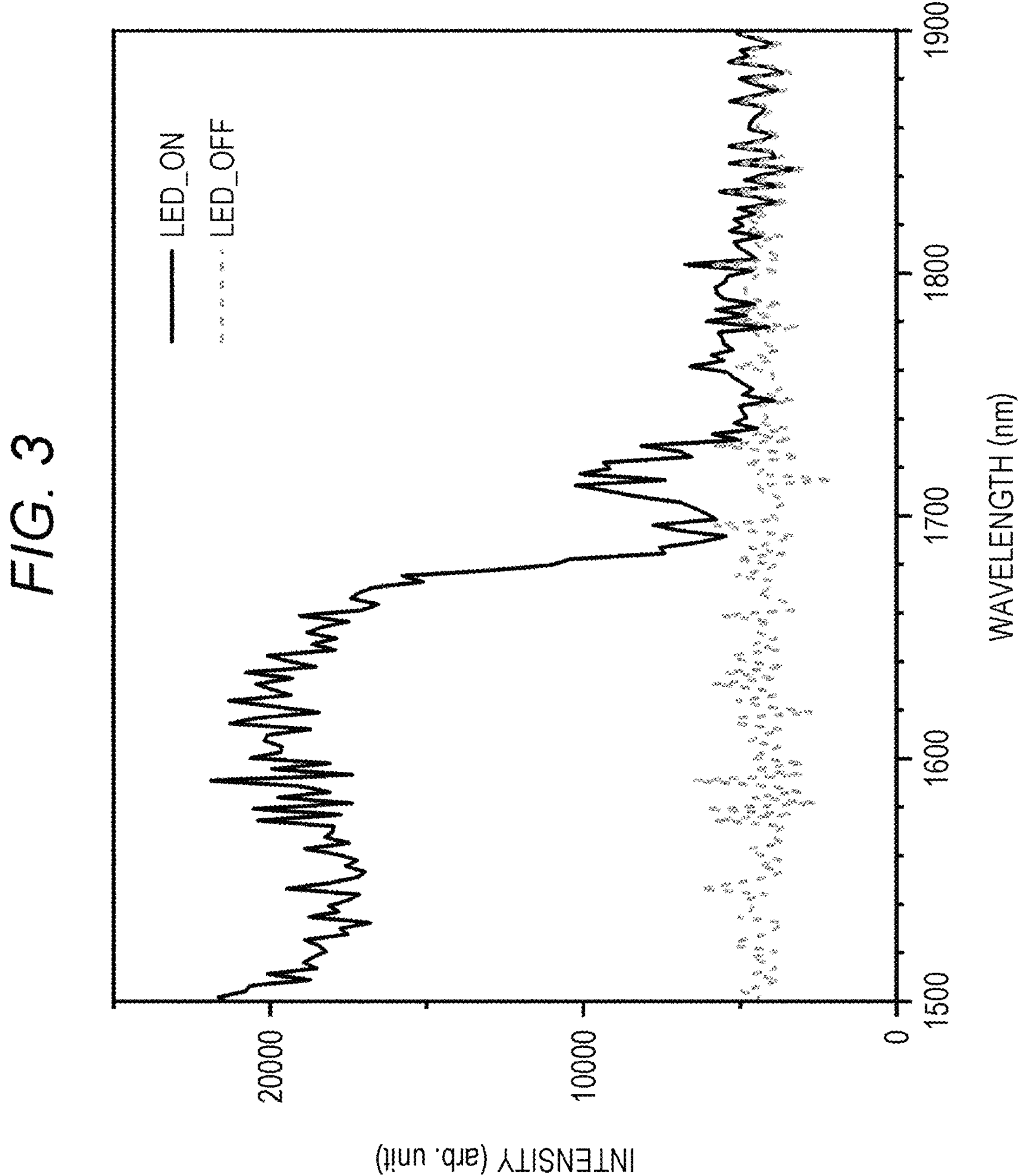
FIG. 3 is a diagram illustrating an example of signal intensity of emission light from an optical cavity when a near-infrared LED light source and a reflector having a reflectivity of 99.5% are employed.

On the other hand, when an LED is used as a light source instead of the laser light source under the condition of using the laser light source, and a reflector having a reflectivity of less than 99.95%, for example, 99.5% is used instead of a reflector having a high reflectivity of 99.99%, an increase in the intensity of the emission light is confirmed as illustrated in FIG. 3. This is considered to be due to the following reason.

As the reflectivity of the reflector decreases, the reflection of the light incident on the optical cavity on the surface of the optical cavity decreases, and the amount of incident light on the optical cavity increases. As a result, the amount of emission light from the optical cavity increases. On the other hand, since the reflectivity of the reflector is low, the number of times of reflection of light in the optical cavity is reduced. Thus, the effective optical path length of the light within the optical cavity is reduced. However, since the amount of emission light from the optical cavity increases, the SN ratio of the detected light is improved, and as a result, absorption of light by the component to be detected can be detected.

Figure 4:
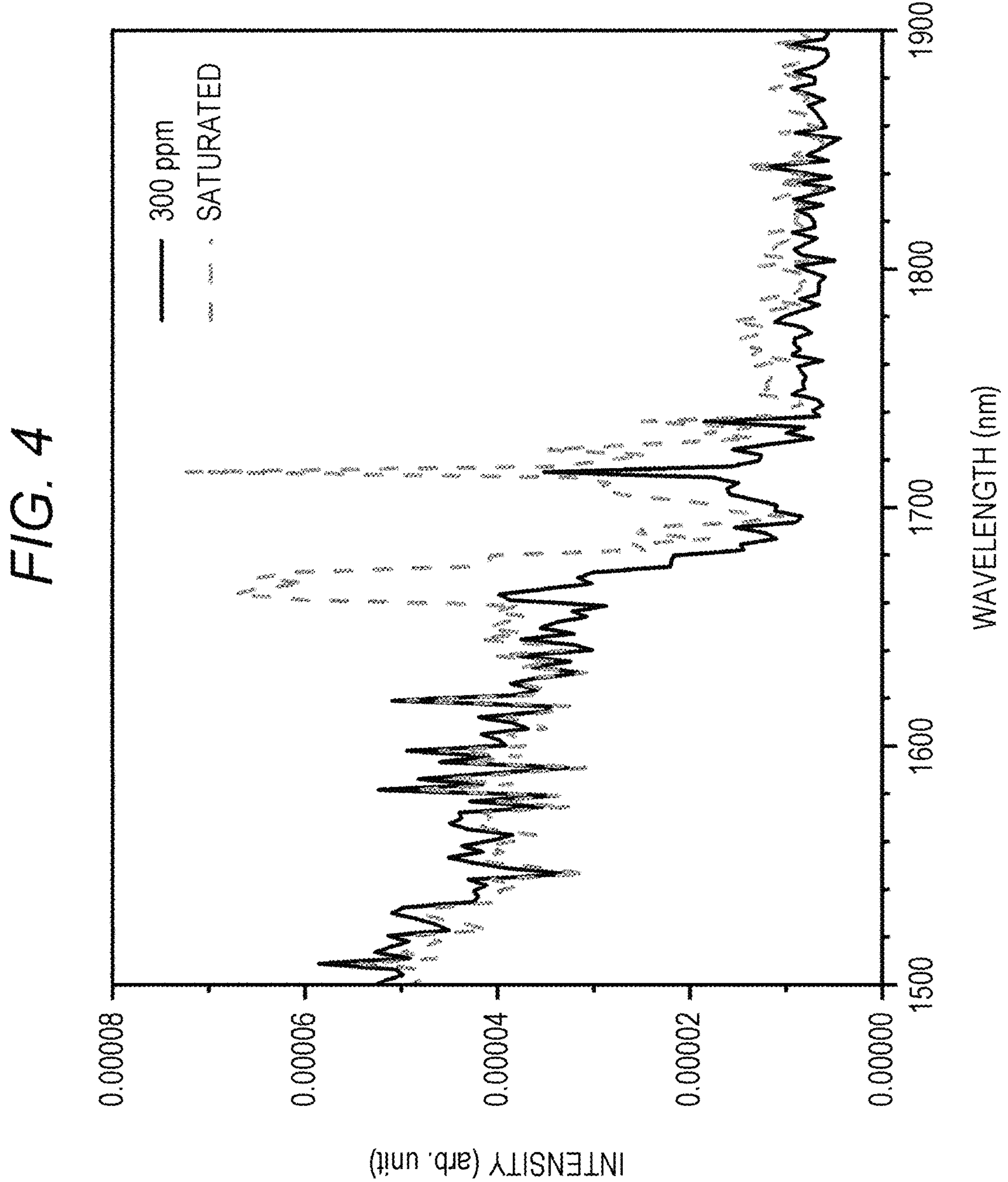
FIG. 4 is a diagram showing an example of signal intensity of emission light from an optical cavity when nitrogen gas containing acetone of 300 ppm in volume (ppmv) is measured by employing a near-infrared LED light source and a reflector having a reflectivity of 99.5%.

Therefore, when nitrogen gas (a component to be detected is acetone) containing 300-ppmv-acetone as an example of the gas to be measured is supplied to the optical cavity in the spectroscopic apparatus under the condition of FIG. 3, and the intensity of the emission light from the optical cavity is detected by the photodetector, a change in the intensity of the signal light is confirmed as illustrated in FIG. 4 (solid line in FIG. 4). In contrast, the inside of the optical cavity is evacuated, and acetone gas having a saturated concentration is introduced, and a change in intensity of the detected signal light is indicated by a broken line in FIG. 4.

Figure 5:
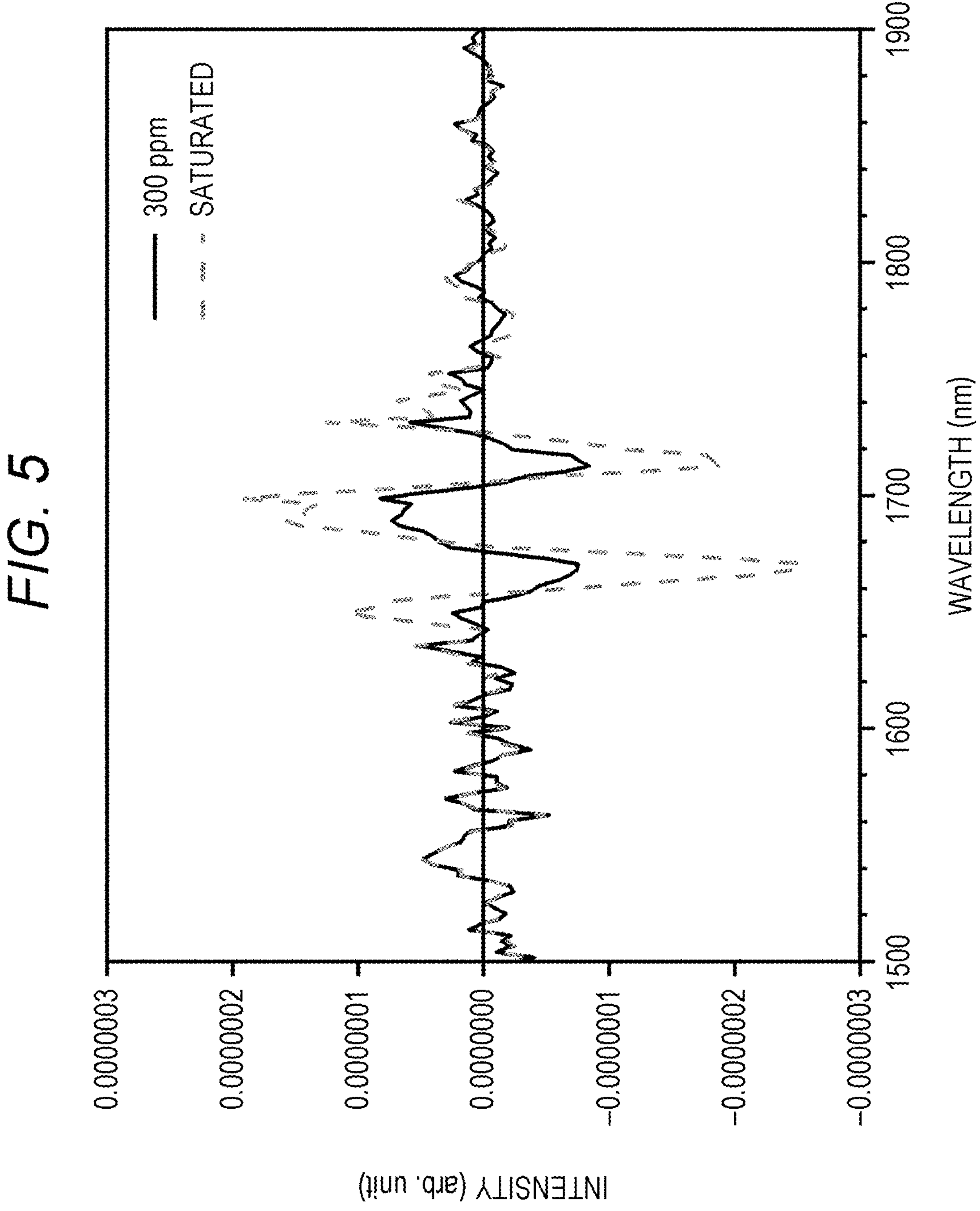
FIG. 5 is a diagram in which a baseline of the graph of FIG. 4 is corrected by second-derivative.

FIG. 5 illustrates a spectrum of the signal light in which the baseline inclined in FIG. 4 is corrected by taking the second-derivative of the spectrum. A solid line in FIG. 5 is the intensity of the signal light of the nitrogen gas containing 300-ppmv-acetone, and a broken line in FIG. 5 is the intensity of the signal light of the acetone gas having a saturated concentration. In the corrected spectrum, a portion where the solid line and the broken line substantially overlap each other and a portion where the broken line swings more largely while the solid line swings less are more clearly confirmed. As can be seen from FIG. 5, the solid line in FIG. 5 includes a peak specific to acetone, and acetone in nitrogen gas containing a trace amount of acetone can be detected by the spectroscopic apparatus.

Figure 6:
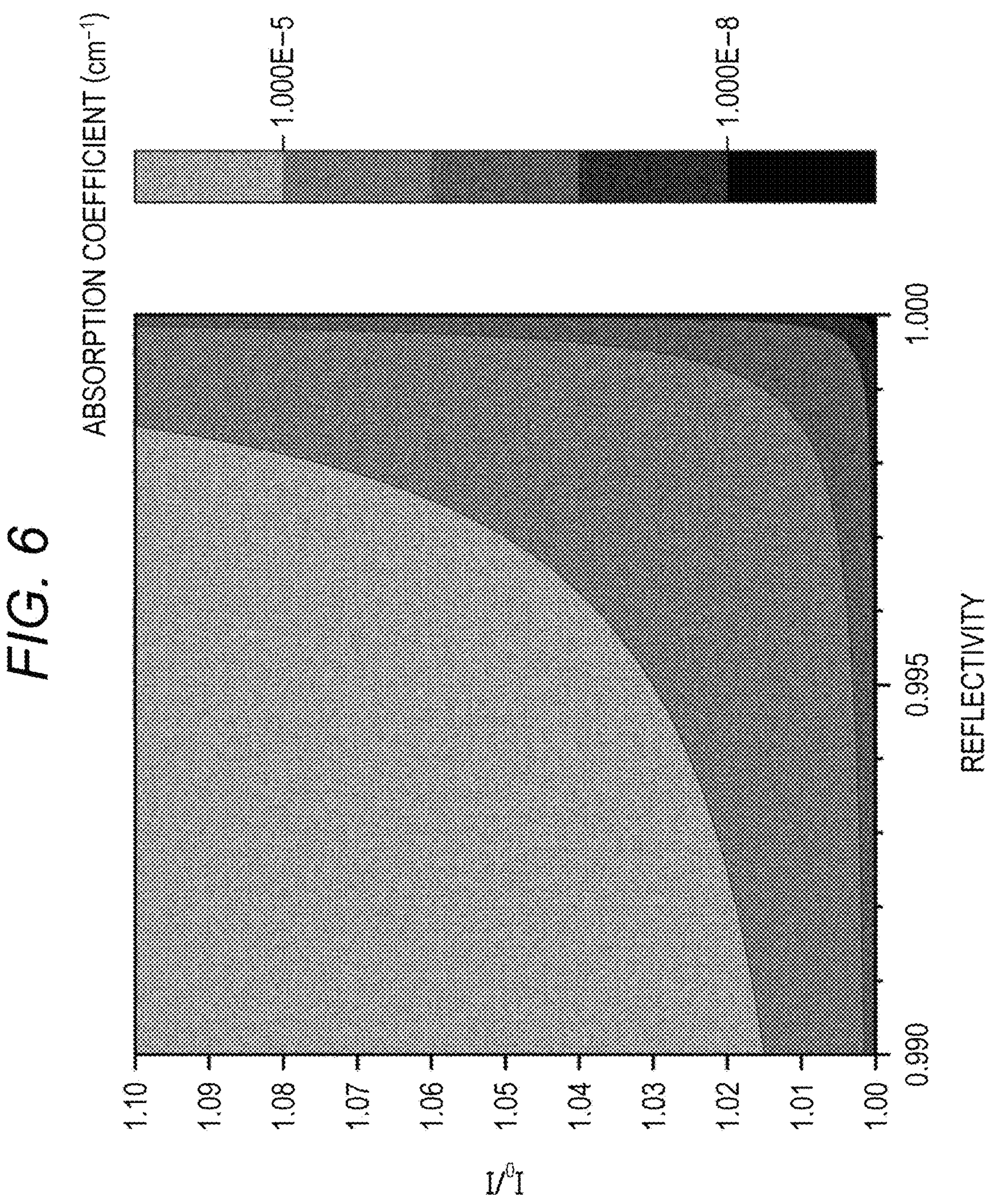
FIG. 6 is a diagram illustrating a relationship among a specific absorption coefficient of acetone, an effective reflectivity of a reflector, and an intensity ratio of signal light at a specific optical-cavity length.

FIG. 6 illustrates a relationship among the absorption coefficient $\alpha$, the effective reflectivity R, and the intensity ratio $I_0/I$ of the signal light when the range of the absorption coefficient $\alpha$ of acetone is a value corresponding to 1-1000 volume ppm and the optical-cavity length is 15 cm. In the drawing, the color is displayed so as to be darker as the absorption coefficient is smaller. In FIG. 6, the region on the side of the darker colored portion than the lightest colored portion is, in effect, the range of the absorption coefficient corresponding to the range in which the acetone concentration contained in the biological gas can change.

According to FIG. 6, when it is recognized that there is a significant difference even in a state where the intensity ratio $I_0/I$ is low (close to 1), that is, when the performance of the photodetector is high, acetone of several 100 ppm in volume can be detected even if the effective reflectivity is low (for example, even at about 0.990-0.995). In addition, according to FIG. 6, it can be seen that acetone of several 100 ppm in volume can be detected even when the effective reflectivity is high (close to 1) and the intensity ratio $I_0/I$ is high (for example, about 1.05-1.10), that is, the performance of the photodetector is low. Furthermore, according to FIG. 6, it is considered that the above tendency is obtained even when the effective reflectivity is less than 0.990 or the intensity ratio $I_0/I$ exceeds 1.10.

From the above, it is found that by setting $\alpha$, L, $I_0$, I, and R so as to satisfy the formula (1) and configuring the spectroscopic apparatus as shown in FIG. 1 that satisfies these conditions, it is possible to detect a trace component in the gas to be measured.

[Specific Aspect of Gas Analysis]

Hereinafter, the analysis of gas in the present embodiment will be described more specifically.

First, an absorption coefficient is set based on species of the gas to be measured (for example, exhaled air), a component to be detected in the gas (for example, the above-described acetone), and a concentration change range of the component to be detected. Furthermore, the reflectors 121 and 122 having effective reflectivities that satisfy the formula (1) are set on the basis of the optical-cavity length of the optical cavity 12 in the spectroscopic apparatus 10. The optical cavity 12 is configured by, for example, arranging a pair of reflectors having an appropriate reflectivity for realizing such an effective reflectivity at both ends thereof.

Next, the intensity $I_0$ of the signal light is measured in a state where the gas to be measured is not supplied to the optical cavity 12. When the intensity $I_0$ under the above conditions is known, the control unit 14 may acquire information of the intensity $I_0$ from the storage unit 143 instead of the measurement.

Next, the measurement gas is supplied to the optical cavity 12 to measure the intensity I of the signal light. The measurement of the intensity I of the signal light may be started by the control unit 14 in response to acquisition of the intensity $I_0$, or may be started by an input signal from the user.

Next, the signal analysis unit 142 calculates an absorption coefficient spectrum from the intensities $I_0$ and I of the signal light. When it is necessary to correct the baseline of the spectrum data, the signal analysis unit 142 corrects the baseline of the spectrum data as described above and transmits the corrected baseline to the display device 30. The display device 30 displays a spectrum as indicated by a solid line in FIG. 5.

Figure 7:
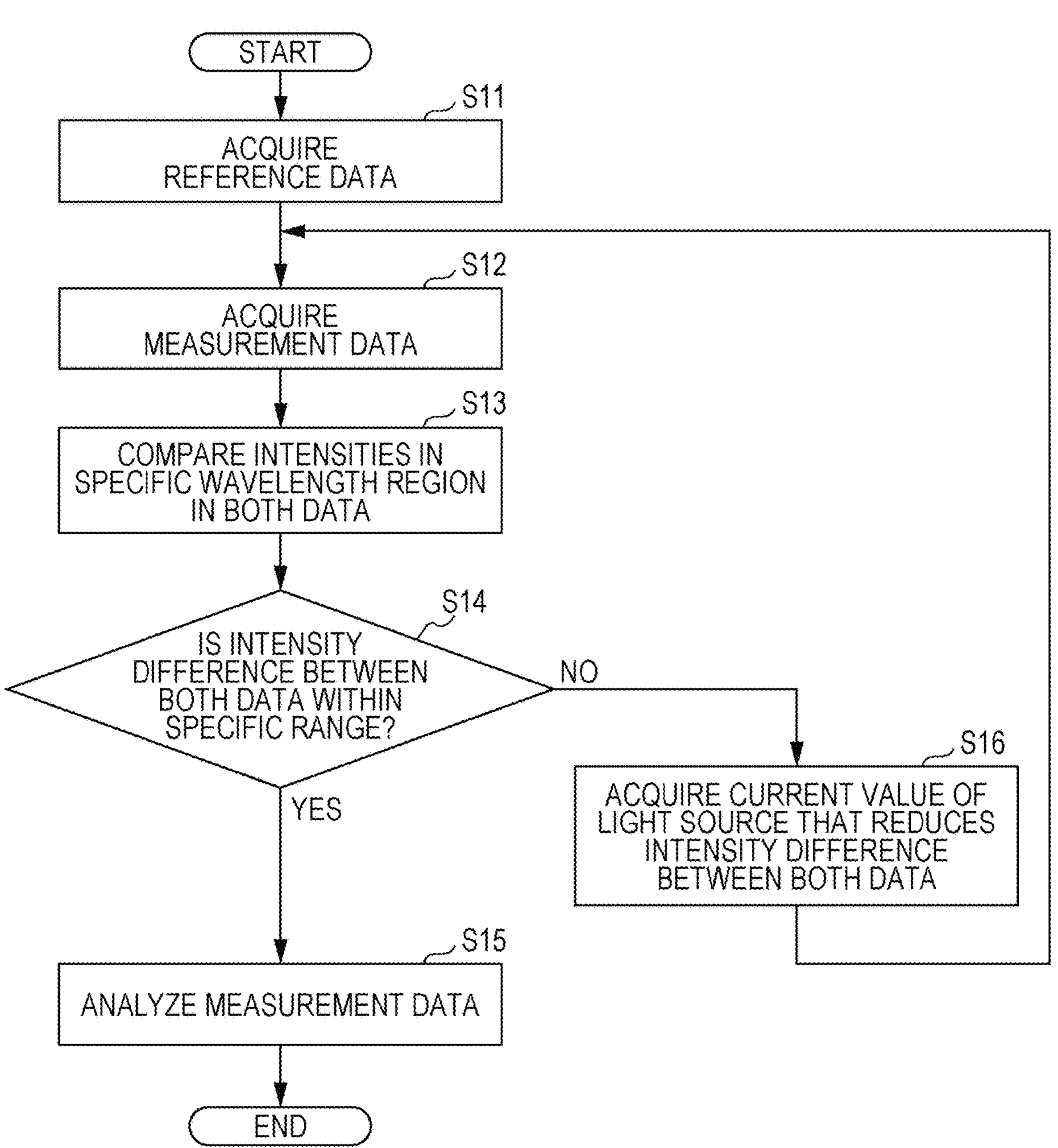
FIG. 7 is a flowchart illustrating an example of a step of correcting the intensity fluctuation of the light source in the first embodiment of the present invention.

In the present embodiment, the control unit 14 corrects the fluctuation of the intensity of the signal light according to the intensity ratio of the signal light. An example of such a gas detection step in the present embodiment is shown in a flowchart of FIG. 7.

In step S11, the control unit 14 acquires reference data. The reference data is known measurement data under the conditions set in the spectroscopic apparatus 10, and may be, for example, previous measurement data under the same conditions stored in the storage unit 143 or first measurement data at the time of the measurement (measurement date).

In step S12, the control unit 14 acquires measurement data.

In step S13, the intensity fluctuation correction unit 141 acquires the reference data and the measurement data, and compares the intensities in a specific wavelength region in both data. The specific wavelength range is a wavelength range that does not substantially include a peak specific to the component to be detected in the measurement wavelength range, and is, for example, a wavelength range in which a solid line and a broken line substantially overlap in FIG. 4 or FIG. 5 described above.

In step S14, the intensity fluctuation correction unit 141 calculates an intensity difference in a specific wavelength region in both data, and determines whether or not the intensity difference is within a specific range.

In a case where the intensity difference is within the specific range in step S14, the signal analysis unit 142 appropriately corrects the measurement data as described above and transmits the corrected measurement data to the display device 30 in step S15.

When the intensity difference exceeds the specific range in step S14, the intensity fluctuation correction unit 141 acquires a corrected output value (current value) of the light source 11 that reduces the intensity difference in step S16, and controls the current value of the light source 11 to the corrected current value. For example, the intensity fluctuation correction unit 141 acquires a current value corrected according to a map of the value of the intensity difference and the correction value corresponding thereto stored in the storage unit 143 in advance. The corrected current value may be a value that makes the intensity difference substantially 0, or may be a value obtained by changing the current value of the light source 11 by a specific value in a direction of reducing the intensity difference.

When the current value of the light source 11 is corrected in step S16, the control unit 14 returns to step S12 and acquires measurement data.

As described above, in the present embodiment, the spectroscopic apparatus 10 includes the intensity fluctuation correction unit 141, detects the fluctuation in the intensity of the emission light detected by the photodetector 13, and outputs the output value of the light source 11 that reduces the fluctuation.

BACKGROUND AND ADVANTAGES OF PRESENT EMBODIMENT

With the aging society becoming more serious, there is an interest in early detection of diseases and daily health observation. However, many medical diagnoses involve pain called invasive diagnosis, and the threshold for medical diagnosis is still high. For example, in diabetes, the blood glucose level of a patient is required to be recorded on a daily basis, which requires the blood of the patient to be collected. In recent years, with the advancement of technology, the pain associated with blood collection has been reduced, but has not been completely removed, and daily diagnosis has become a great stress for patients. Furthermore, there is also a problem such as a risk of infection. From these backgrounds, there is a high demand for non-invasive diagnosis capable of performing diagnosis with no pain without damaging the human body.

On the other hand, a correlation between a specific gas component in a biological gas such as exhaled air and a medical condition has been reported. That is, as the specific medical condition progresses, the concentration of the specific gas component increases or decreases. Therefore, if the concentration of a specific gas component can be quantitatively evaluated, it can be applied to diagnosis of a specific medical condition. The biological gas can be collected as a sample for diagnosis without giving pain to the patient. Also from such a viewpoint, application of analysis of biological gas to non-invasive diagnosis is expected. However, it is technically difficult to quantitatively evaluate only a specific component as a target.

Such technical difficulties include measurement fluctuations. In a general light source, the intensity of emission light fluctuates during driving (intensity fluctuation). When the intensity of light for measurement fluctuates during measurement, it becomes difficult to distinguish between such intensity fluctuation and a change due to signal light. Therefore, it is important to suppress the intensity fluctuation particularly when an extremely small signal such as measurement of a trace amount of biological gas is captured. In addition, it is known that a center wavelength of an emission spectrum of a semiconductor laser and an LED is shifted by a temperature of an element (wavelength fluctuation). When a wavelength shift occurs during measurement, the light source intensity at each wavelength fluctuates, and the light source spectrum differs between the reference data and the measurement data, which may cause an unintended false signal. Therefore, it is important to suppress these fluctuations in performing quantitative evaluation. However, conventionally, studies on a mechanism for suppressing such fluctuations have not been confirmed, and it can be said that there is room for studies in the prior art from the viewpoint of countermeasures against the fluctuations.

In such a technical or social background, as is clear from the above description, the spectroscopic apparatus 10 of the present embodiment introduces biological gas emitted from a human body such as exhaled air or skin gas into the optical cavity 12 constructed by facing the two reflectors 121 and 122 having a specific reflectivity, irradiates the optical cavity 12 with light (near-infrared light) emitted from the light source 11, and detects the spectral intensity of the light leaking from the optical cavity 12. In addition, the gas detection apparatus of the present embodiment quantitatively evaluates a specific component (for example, the above-described acetone) in the biological gas from the spectral intensity.

The spectroscopic apparatus 10 includes a light source 11 that outputs near-infrared light, and a full width at half maximum of a wavelength spectrum of the near-infrared light that is output from the light source 11 and enters the optical cavity 12 is 15 nm or more. Therefore, since it is only required to reciprocate in the optical cavity 12 under the condition that the component of any wavelength in the incident light on the optical cavity 12 becomes a stationary wave, the alignment accuracy of the optical-cavity length can be lowered as compared with the case of adopting the laser light source. Therefore, it is not necessary to strictly adjust the optical-cavity length, and a configuration therefor (for example, a piezo stage) is unnecessary.

More specifically, in the spectroscopic apparatus 10, the cost can be suppressed as compared with the case of adopting the laser light source. That is, by using a light source that is cheaper than a laser light source such as a near-infrared LED light source as the light source 11, it is possible to suppress the product cost of the spectroscopic apparatus 10.

In addition, in the conventional case of adopting the laser light source, as described above, highly accurate optical axis adjustment and optical-cavity length control are required, and accordingly, a component for optical axis adjustment and a piezo stage for adjusting the optical-cavity length are required. Furthermore, since it is weak against mechanical vibration, a component for vibration suppression is required. These incidentally required parts also increase the product cost of the analysis device. On the other hand, in the present embodiment, by using the light source 11 having a broadband as compared with the laser light source, it is not necessary to strictly adjust the resonance condition with the optical cavity 12, and it is not necessary to perform highly accurate optical axis adjustment and highly accurate control of the optical-cavity length. Therefore, the above-described expensive parts and the like are unnecessary, which leads to a reduction in product cost.

In addition, in the present embodiment, since the wavelength region of the incident light to the optical cavity 12 has a specific spread, it is less susceptible to the influence of disturbance than the case of adopting the laser light source.

Furthermore, in the present embodiment, it is possible to acquire a spectrum within the wavelength range by one measurement. Therefore, measurement can be performed in a short time with one light source 11. In the conventional case of using a laser light source, only single-wavelength data can be obtained in basically one measurement from resonance conditions with the optical cavity. In a conventional technique (see JP 2005-501233 A) in which data (spectrum) of a plurality of wavelengths is obtained by using a wavelength-tunable laser light source, it is necessary to adjust an optical-cavity length with a piezo stage or the like every time the wavelength is changed. Therefore, the overall measurement time becomes enormous. In the present embodiment, since a broadband light source is used as compared with a laser light source, a spectrum can be obtained by one measurement. Therefore, the measurement time can be significantly shortened.

In addition, the pair of reflectors 121 and 122 of the spectroscopic apparatus 10 has an effective reflectivity that satisfies the formula (1) described above. Therefore, the optical cavity 12 can be constructed by adopting a reflector having a reflectivity of less than 99.95% as the reflector, and cavity-enhanced absorption spectrometry can be realized even with the light source 11 having a low output. In general, the effective optical path length becomes longer as the reflectivity of the reflector is higher, but at the same time, the amount of light entering the optical cavity and the amount of light leaking from the optical cavity become smaller. Therefore, in the case of constructing an optical cavity using a high-reflectivity mirror of 99.95% or more, it is practically required to use a high-output light source such as a laser light source in order to obtain a detectable sufficient amount of light (see JP 2016-502077 A).

In the present embodiment, an appropriate reflectivity range of the reflectors 121 and 122 is set from the concentration change range of the biological gas component to be detected, and the optical cavity 12 can be designed. In addition, a photodetector 13 having detection sensitivity that satisfies the formula (1) is applied. This makes it possible to construct the optical cavity 12 even with the reflectors 121 and 122 having a reflectivity of less than 99.95%, and a light source 11 having a lower output than a light source other than the laser light source, for example, a laser light source such as an LED light source can be used for cavity-enhanced absorption spectroscopy.

Furthermore, in the present embodiment, since it is not necessary to control the optical-cavity length, a device configuration without a movable portion in the optical cavity 12 is possible, and a maintenance-free product can be realized.

In addition, the spectroscopic apparatus 10 further includes an intensity fluctuation correction unit 141. As described above, in the present embodiment, by incorporating a mechanism that suppresses the intensity fluctuation of the light source 11, noise during measurement can be reduced, and measurement with higher accuracy can be realized. Such suppression of the intensity fluctuation can be suitably realized by current feedback that refers to the signal intensity of the photodetector 13 and adjusts the current applied to the light source 11 from the signal intensity.

Second Embodiment

Figure 8:
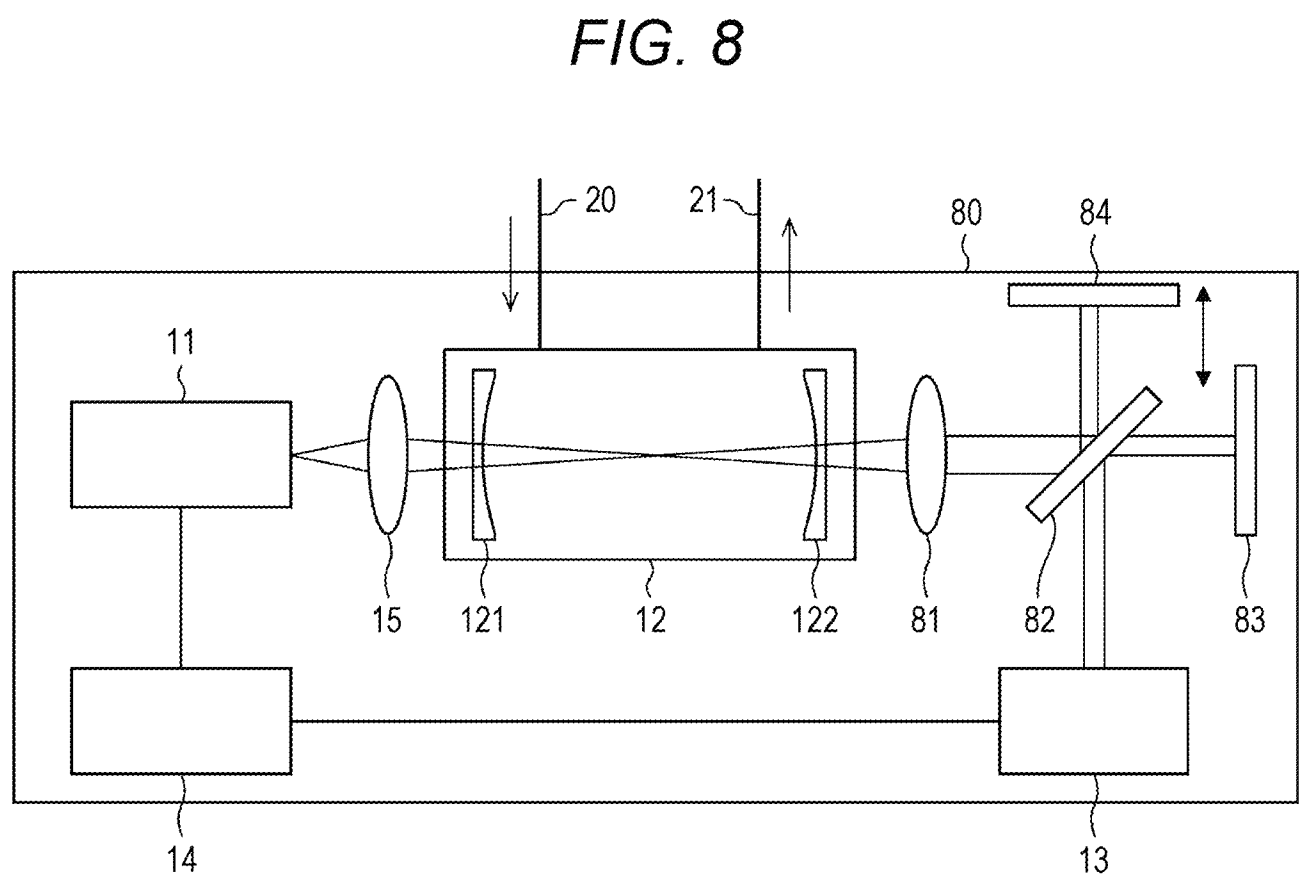

Hereinafter, another embodiment of the present invention will be described. In the following embodiment, for convenience of description, members having the same functions as the members in the above-described embodiment are denoted by the same reference numerals, and description thereof will not be repeated. As illustrated in FIG. 8, the spectroscopic apparatus 80 of the present embodiment is configured similarly to the spectroscopic apparatus 10 of the first embodiment described above except for the configuration described below.

The spectroscopic apparatus 80 includes a collimator lens 81 for outputting emission light from the optical cavity 12 as parallel light instead of the focus lens 16, and includes a beam splitter 82 for dividing the parallel light instead of the diffraction grating 17. Furthermore, the spectroscopic apparatus 80 further includes a reflector 83 that reflects a first component of the parallel light transmitted through the beam splitter 82, and a reflector 84 that reflects a second component of the parallel light reflected and divided by the beam splitter 82. The reflector 84 is supported by a movable stage (not illustrated) movable by a double-headed arrow in the drawing, and is movable by the double-headed arrow in the drawing.

The light having the interference pattern is detected by the photodetector 13 by sweeping the movable stage. The control unit 14 (signal analysis unit 142) performs Fourier transform on the signal of the interference pattern detected by the photodetector 13. Thus, a spectrum substantially equivalent to that of the spectroscopic apparatus 10 including the diffraction grating 17 is obtained.

The present embodiment has the same effects as those of the first embodiment described above. Since the present embodiment uses the interference pattern, the loss of the signal light due to the diffraction grating does not substantially occur. Therefore, almost all the signal light can be detected. Therefore, the present embodiment is advantageous from the viewpoint of detecting weak light.

Third Embodiment

Figure 9:
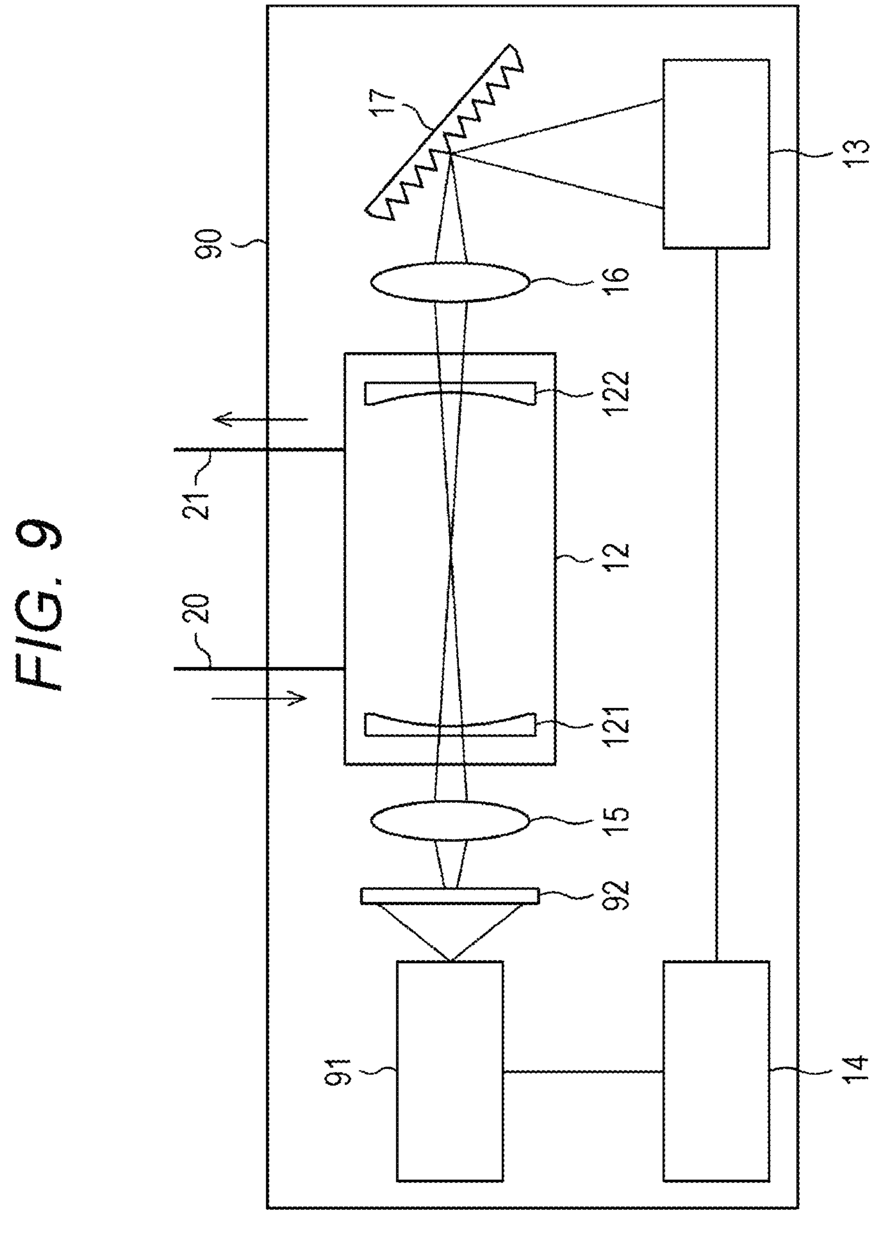
FIG. 9 is a diagram schematically illustrating a configuration of a spectroscopic apparatus according to the third embodiment of the present invention.

As illustrated in FIG. 9, the spectroscopic apparatus 90 of the present embodiment is configured similarly to the spectroscopic apparatus 10 of the first embodiment described above except for the configuration described below.

The spectroscopic apparatus 90 includes a light source 91 that is a halogen lamp instead of the light source 11, and a band pass filter 92 that transmits only a light component having a specific wavelength region among the emission light from the light source 91. Even with such a configuration, a light source having a low output but being inexpensive compared to a laser light source is used, and the same near-infrared light as in the first embodiment can be introduced into the optical cavity 12. The present embodiment also has the same effects as those of the first embodiment described above. In the present embodiment, measurement can be performed at an arbitrary wavelength only by switching the transmission wavelength of the band pass filter without preparing a plurality of light sources. Therefore, the present embodiment is advantageous from the viewpoint of enabling measurement of a plurality of components to be detected with the same device.

Fourth Embodiment

Figure 10:
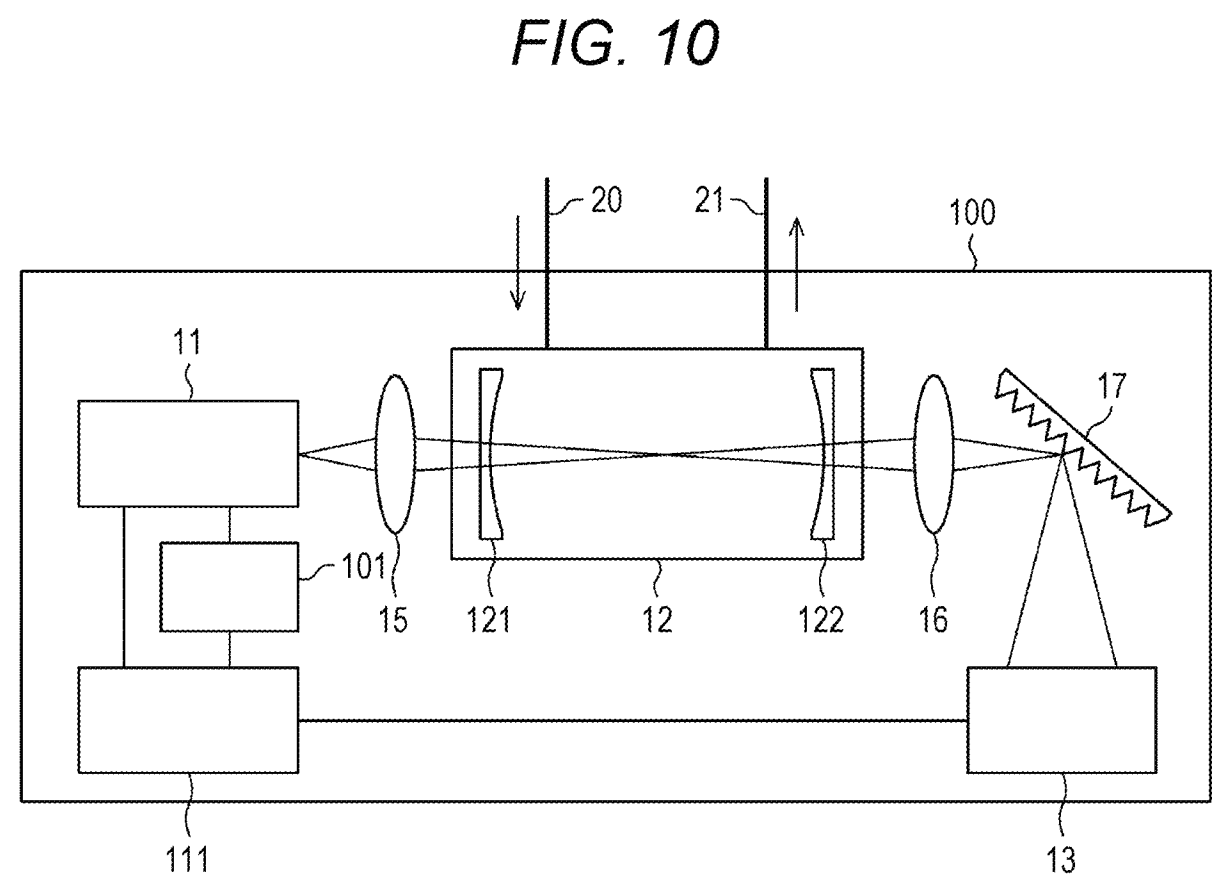

As illustrated in FIG. 10, the spectroscopic apparatus 100 of the present embodiment is configured similarly to the spectroscopic apparatus 10 of the first embodiment described above except that it further includes a temperature adjustment device 101 that adjusts the internal temperature of the optical cavity 12. The temperature adjustment device 101 is, for example, a heating device such as a thermocouple, and is disposed at or near the light source 11 to adjust the temperature of the light source 11. The control unit 14 operates the temperature adjustment device 101 so that the temperature of the light source 11 is maintained at a constant temperature or a specific temperature range. In the present embodiment, the temperature of the light source 11 is kept constant.

The present embodiment also has the same effects as those of the first embodiment described above. In the present embodiment, since the influence of the temperature disturbance on the light source 11 is further suppressed, the wavelength fluctuation of the emission light of the light source 11 is further suppressed. Therefore, the present embodiment is more effective from the viewpoint of reducing noise during measurement due to wavelength fluctuations and realizing measurement with higher accuracy.

Fifth Embodiment

Figure 11:
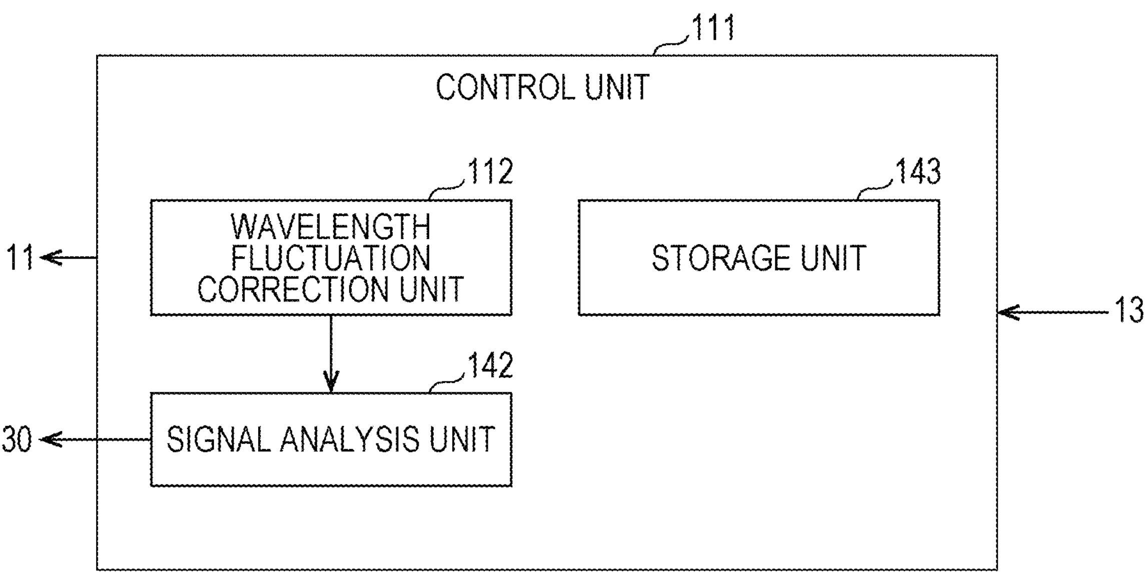
FIG. 11 is a diagram schematically illustrating an example of a functional configuration of a control unit in the fifth embodiment of the present invention.

The spectroscopic apparatus of the present embodiment is configured similarly to the spectroscopic apparatus 10 of the first embodiment described above except that a control unit 111 illustrated in FIG. 11 is included instead of the control unit 14. The control unit 111 is configured similarly to the control unit 14 of the first embodiment described above except that a wavelength fluctuation correction unit 112 is provided instead of the intensity fluctuation correction unit 141.

Figure 12:
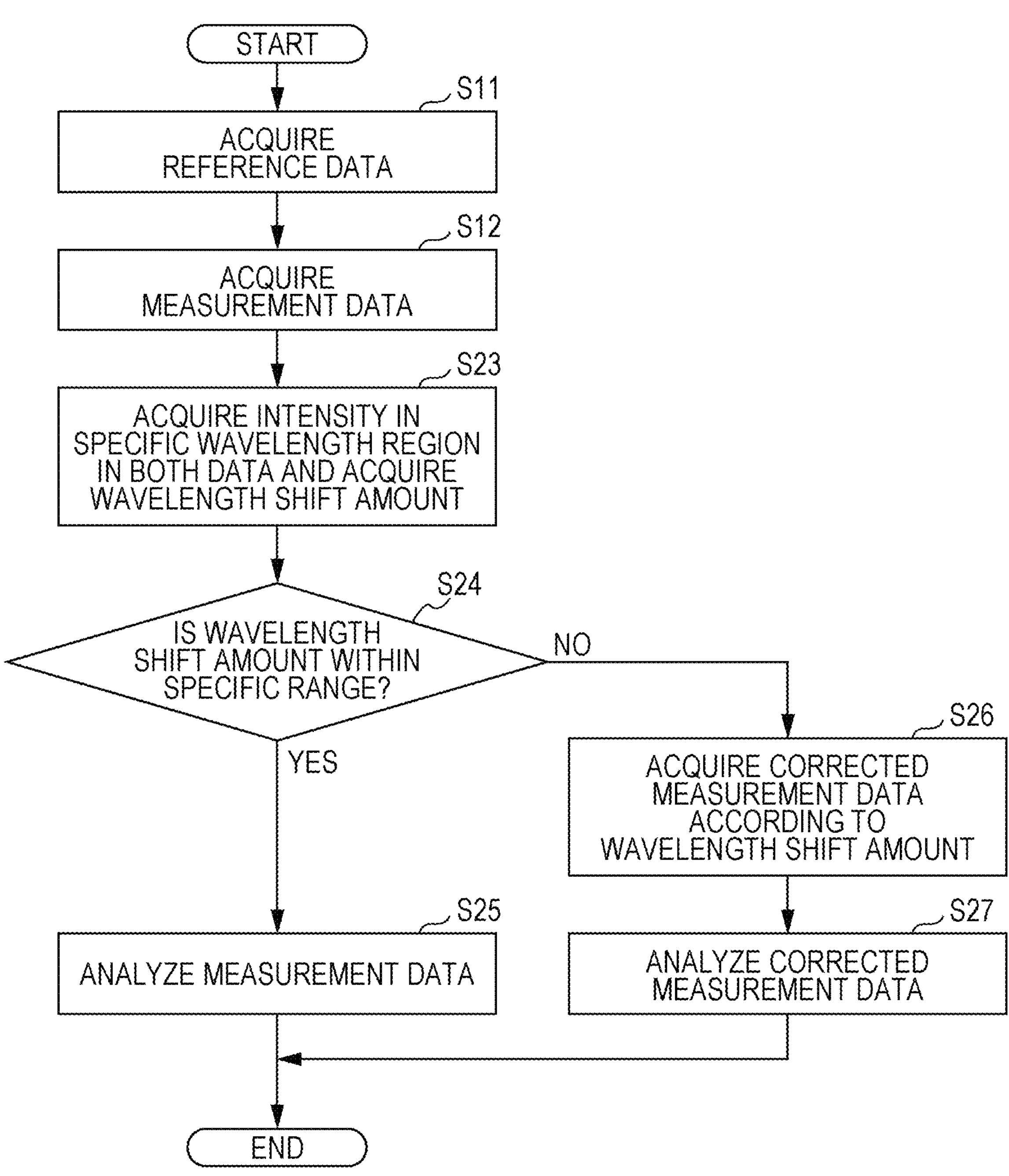
FIG. 12 is a flowchart illustrating an example of a step of correcting the wavelength fluctuation of the light source in the fifth embodiment of the present invention.

The wavelength fluctuation correction unit 112 detects fluctuation in wavelength of the emission light detected by the photodetector 13 and corrects a detection value of the emission light based on the fluctuation. An example of a process of correcting such wavelength fluctuation of the light source in the present embodiment is illustrated in a flowchart of FIG. 12.

Steps S11 and 12 are similar to those in the first embodiment described above.

In step S23, the wavelength fluctuation correction unit 112 acquires the reference data and the measurement data, and acquires the intensity in a specific wavelength region in both data. The specific wavelength range is the same as that of the first embodiment, and is a wavelength range that does not substantially include a peak specific to the component to be detected in the measurement wavelength range. The wavelength fluctuation correction unit 112 acquires, for example, data of the light source spectrum at each temperature stored in advance in the storage unit 143 as reference data. Then, the wavelength fluctuation correction unit 112 acquires the shift amount of the wavelength from the relative intensity in these data.

In step S24, the wavelength fluctuation correction unit 112 determines whether or not the acquired shift amount of the wavelength is within a specific range.

When the shift amount of the wavelength is within the specific range in step S24, the signal analysis unit 142 transmits the measurement data to the display device 30 in step S25 in the same manner as in the first embodiment.

When the shift amount of the wavelength exceeds the specific range in step S24, the wavelength fluctuation correction unit 112 corrects the measurement data according to the shift amount of the wavelength in step S26. For example, the wavelength fluctuation correction unit 112 performs correction to shift the wavelength information of the measurement data in a direction of canceling the shift amount according to the shift amount.

In step S27, the signal analysis unit 142 acquires the measurement data corrected in step S26, and transmits the measurement data to the display device 30 as in the first embodiment.

As described above, the present embodiment employs a system in which a wavelength shift amount due to wavelength fluctuation in measurement data is calculated from the relative intensity between arbitrary wavelengths that do not contribute to absorption of biological gas on the spectrum in the measurement data and the reference data, and calculation for correcting the wavelength shift amount is performed on the measurement result. The present embodiment exhibits the same effect as that of the first embodiment described above except that the effect of suppressing the wavelength fluctuation of the light source 11 is exhibited instead of the effect of suppressing the intensity fluctuation of the light source 11.

Other Embodiments

In the above-described embodiment, the reflectivity of near-infrared light of one of the pair of reflectors closer to the light source in an optical path of near-infrared light from the light source may be equal to or greater than a reflectivity of near-infrared light of the other reflector. In a case where the light source, the optical cavity, and the photodetector are sequentially arranged along the optical path of the near-infrared light from the light source, one of the reflectors is a reflector arranged on the light source side, and the other reflector is a reflector arranged facing the one of the reflectors. Each of the reflectors is a reflector that transmits a part of incident light and reflects the rest of the incident light. Light that reaches the back surface of one of the reflectors from the light source and transmits is incident light to the optical cavity, and light that transmits through the other of the reflectors is emission light from the optical cavity. The present embodiment is more effective from the viewpoint of increasing the amount of emission light from the optical cavity.

In the above-described embodiment, the light source may be a thermal radiation light source as long as the light source has a low output but is inexpensive as compared with a laser light source.

In the foregoing embodiment, the display device may further include a touch panel. In this case, the display device also serves as an input device by the user, and the control unit can control the operation of the spectroscopic apparatus according to the input signal from the display device.

In the above-described embodiment, the control unit may further include a communication unit that transmits data. In this case, data acquired by the analysis device is transmitted to a user, a specific computer, or a cloud server, and can be applied to various applications such as analysis of gas to be measured, diagnosis based on the analysis, or machine learning using the data as teacher data. In addition, the above aspect is advantageous from the viewpoint of making the analysis device and the gas detection apparatus of the present invention compact, improving the portability, and improving the convenience of the detection of the gas to be measured.

In the above-described embodiment, the optical cavity may have a configuration other than the above-described configuration. For example, the optical cavity may include a first reflector that partially transmits light to the light source side of the optical path and reflects the rest, and a second reflector that is disposed opposite to the first reflector and substantially totally reflects light. In this case, the spectroscopic apparatus preferably includes an optical system that directs the emission light from the first reflector toward the photodetector from the viewpoint of appropriately setting the optical path in the spectroscopic apparatus.

In the foregoing embodiments, the optical cavity may not have a gas supply unit. For example, the optical cavity may be subjected to spectroscopic analysis by the spectroscopic apparatus in a state where the gas to be measured is enclosed (for example, in a state where the biological gas has already been sampled).

In the foregoing embodiments, the optical cavity may be configured to have an adjustable optical-cavity length. Alternatively, in the foregoing embodiment, one or both reflectors in the pair of reflectors may be exchangeable as appropriate. Such a configuration is suitable for examining conditions (Type, density, intensity ratio and effective reflectivity of signal light, and the like) under which the component to be detected can be measured, and is suitable from the viewpoint of enhancing the versatility of the spectroscopic apparatus.

In the above-described embodiment, when a plurality of components to be detected are included in the gas to be measured, the detection data of each component can be appropriately acquired by differentiating the spectrum data to separate the peak and correcting the baseline. In the above-described embodiment, the control unit may perform such separation processing of the plurality of pieces of spectrum data.

In the foregoing embodiments, the spectroscopic apparatus or gas detection apparatus may be utilized for examination of a patient, such as identification of a medical condition for which a correlation with a particular component in the biological gas for which a relationship with the medical condition has been reported has been reported. Alternatively, in the above-described embodiment, the measurement may be performed for a trace component (hazardous material or the like) in the gas to be measured other than the biological gas.

[Example of Implementation by Software]

The function of the spectroscopic apparatus (hereinafter, also referred to as "apparatus") in the above-described embodiment is a program for causing a computer to function as the apparatus, and can be realized by a program for causing a computer to function as each control block of the apparatus (in particular, each unit included in the control unit 14 and the like).

In this case, the device includes a computer that has at least one control device (for example, a processor) and at least one storage device (for example, a memory) as hardware for executing the program. The control device and the storage device execute the program to implement each function described in each of the above-described embodiments.

The program may be recorded on one or more non-transitory computer-readable recording media. This recording medium may or may not be included in the device. In the latter case, the program may be supplied to the device through any wired or wireless transmission medium.

In addition, some or all of the functions of the control blocks can be realized by a logic circuit. For example, an integrated circuit in which a logic circuit functioning as each control block is formed is also included in the scope of the present invention. In addition, for example, the functions of the control blocks can be realized by a quantum computer.

In addition, each processing described in above the embodiments may be executed by artificial intelligence (AI). In this case, the AI may operate in the control device, or may operate in another device (for example, an edge computer, a cloud server, or the like).

The present invention is not limited to the above-described embodiments, and various modifications can be made within the scope of the claims. Embodiments obtained by combining as appropriate technical means disclosed in relation to different embodiments are also included in the technical scope of the present invention.

SUMMARY

According to a first aspect of the present invention, a spectroscopic apparatus (10) includes: a light source (11) that outputs near-infrared light; an optical cavity (12) that has a pair of opposing reflectors (121, 122) and can supply a gas to be measured between the reflectors, and in which incident light from the light source is introduced into between the reflectors; and a photodetector (13) that detects intensity of emission light from the optical cavity for each wavelength, in which a full width at half maximum of a wavelength spectrum of near-infrared light output from the light source and incident on the optical cavity is 15 nm or more, and the spectroscopic apparatus satisfies the following formula (1) in a specific concentration change range of the gas to be measured. In the formula (1), a represents an absorption coefficient of the gas to be measured, L represents a distance between optical centers of the pair of reflectors, $I_0$ represents the intensity of the emission light from the optical cavity when the gas to be measured is not supplied to the optical cavity, I represents the intensity of the emission light from the optical cavity to which the gas to be measured is supplied, and R represents an effective reflectivity of the pair of reflectors represented by the formula (2), and in the formula (2), R1 represents the reflectivity of one of the pair of reflectors, and R2 represents the reflectivity of the other of the pair of reflectors. According to the first aspect, it is possible to provide a technique for detecting a trace gas that suppresses an increase in cost and is highly practical.

[Math 6]

$$\alpha = \frac{1}{L}\left(\frac{I_0}{I} - 1\right)(1 - R) \quad (1)$$

$$R = \sqrt{R1 \times R2} \quad (2)$$

The second aspect of the present invention further includes, in the first aspect, an intensity fluctuation correction unit (141) that detects fluctuation in intensity of the emission light detected by the photodetector and outputs an output value of the light source that reduces the fluctuation. The second aspect is more effective from the viewpoint of improving the accuracy in analysis.

The third aspect of the present invention further includes, in the first or second aspect, a wavelength fluctuation correction unit (112) that detects wavelength fluctuation of emission light detected by the photodetector and corrects a detection value of the emission light on the basis of the fluctuation. The third aspect is more effective from the viewpoint of improving the accuracy in analysis.

According to a fourth aspect of the present invention, in any one of the first to third aspects, a reflectivity of near-infrared light in each of the pair of reflectors is less than 99.95%. The fourth aspect is still more effective from the viewpoint of making a light source having a lower output than a laser light source available for cavity-enhanced absorption spectroscopy.

A fifth aspect of the present invention according to any one of the first to fourth aspects further includes a temperature adjustment device (101) that adjusts the temperature of the light source. The fifth aspect is more effective from the viewpoint of improving the accuracy in analysis.

According to a sixth aspect of the present invention, in any one of the first to fifth aspects, a reflectivity of near-infrared light of one of the pair of reflectors closer to the light source in an optical path of near-infrared light from the light source is equal to or greater than a reflectivity of near-infrared light of the other reflector. The sixth aspect is more effective from the viewpoint of increasing the amount of emission light from the optical cavity.

A seventh aspect of the present invention is a gas detection apparatus (1) including: the spectroscopic apparatus according to any one of the first to sixth aspects; and a gas supply unit (20) that supplies a gas to be measured to an optical cavity. According to the seventh aspect, similarly to the first aspect described above, it is possible to provide a technique for detecting a trace gas that suppresses an increase in cost and is highly practical.

According to the present invention, it is possible to easily detect a trace component in a gas, such as a specific component related to a disease in a biological gas, with an inexpensive configuration as compared with the related art. The present invention having such effects is expected to contribute to the achievement of the goals 3 and 9 of the United Nations' sustainable development goals (SDGs), "ensure healthy lives and promote well-being for all at all ages" and "Build resilient infrastructure, promote inclusive and sustainable industrialization and foster innovation".

What is claimed is:

1. A spectroscopic apparatus comprising:

a light source that outputs near-infrared light;

an optical cavity that has a pair of opposing reflectors and can supply a gas to be measured between the reflectors, and in which incident light from the light source is introduced into between the reflectors; and a photodetector that detects intensity of emission light from the optical cavity for each wavelength, wherein a full width at half maximum of a wavelength spectrum of near-infrared light output from the light source and incident on the optical cavity is 15 nm or more, and the spectroscopic apparatus satisfies the following formula (1) in a specific concentration change range of the gas to be measured:

[Math 1]

$$\alpha = \frac{1}{L}\left(\frac{I_0}{I} - 1\right)(1 - R) \quad (1)$$

$$R = \sqrt{R1 \times R2} \quad (2)$$

in the formula (1), α represents an absorption coefficient of the gas to be measured, L represents a distance between optical centers of the pair of reflectors, $I_0$ represents the intensity of the emission light from the optical cavity when the gas to be measured is not supplied to the optical cavity, I represents the intensity of the emission light from the optical cavity to which the gas to be measured is supplied, and R represents an effective reflectivity of the pair of reflectors represented by the formula (2), and in the formula (2), R1 represents the reflectivity of one of the pair of reflectors, and R2 represents the reflectivity of the other of the pair of reflectors.

2. The spectroscopic apparatus according to claim 1, further comprising an intensity fluctuation correction unit that detects fluctuation in intensity of the emission light detected by the photodetector and outputs an output value of the light source that reduces the fluctuation.

3. The spectroscopic apparatus according to claim 1, further comprising a wavelength fluctuation correction unit that detects fluctuation in wavelength of the emission light detected by the photodetector and corrects a detection value of the emission light based on the fluctuation.

4. The spectroscopic apparatus according to claim 1, wherein a reflectivity of near-infrared light in each of the pair of reflectors is less than 99.95%.

5. The spectroscopic apparatus according to claim 1, further comprising a temperature adjustment device that adjusts a temperature of the light source.

6. The spectroscopic apparatus according to claim 1, wherein a reflectivity of near-infrared light of one of the pair of reflectors closer to the light source in an optical path of near-infrared light from the light source is equal to or greater than a reflectivity of near-infrared light of the other reflector.

7. A gas detection apparatus comprising: the spectroscopic apparatus according to claim 1; and a gas supply unit that supplies the gas to be measured to the optical cavity.

* * * * *